United States Patent [19]

Sakagami et al.

[11] Patent Number: 4,985,249

[45] Date of Patent: Jan. 15, 1991

[54] ANTI-HIV AGENTS

[76] Inventors: Hiroshi Sakagami; Kunio Konno; Meihan Nonoyama, all of c/o Medical Department, Showa University of 1-5-8, Hatanodai, Shinagawa-ku, Tokyo, Japan

[21] Appl. No.: 209,926

[22] Filed: Jun. 22, 1988

[30] Foreign Application Priority Data

Jun. 26, 1987 [JP] Japan .................................. 62-159423
Mar. 19, 1988 [JP] Japan .................................. 63-662252

[51] Int. Cl.$^5$ .............................................. A61K 35/78
[52] U.S. Cl. .................................... 424/195.1; 514/54; 514/934
[58] Field of Search ................. 424/195.1; 514/54, 934

[56] References Cited

PUBLICATIONS

Chem. Abst. 110(9): 69032u, 1989.
Chem. Abst. 109(15): 12535; 1988.
(1) "Partial Purification of Various Active Substances from Pine Cone Extract of Pinus Parviflora Seib. et Zucc" (abst. 109: 125935j) (published on Dec. 28, 1987).
(2) "Spontaeous Production of Differentiation-Inducing Factor(s) by Mouse Macrophage-Like Cell Line" (abst. 110; 69032u) (published Aug. 28, 1988).
Biological Abstracts, vol. 81, No. 12, 1986, No. 113512, Sakagami et al.
Chemical Abstracts, vol. 78, No. 19, 14th May 1973, p. 70, No. 119653r, Joubert et al.

*Primary Examiner*—John W. Rollins
*Attorney, Agent, or Firm*—Oliff & Berridge

[57] ABSTRACT

Anti-HIV agent containing as active components alkaline water extracts of pine cone and method for producing high molecular weight substance having anti-HIV activity.

11 Claims, 4 Drawing Sheets

ANTI-HIV AGENTS

BACKGROUND OF THE INVENTION

The present invention relates to plant-derived high molecular weight substances which have potent anti-HIV activity. The human immunodeficiency virus (HIV) is the causative agent associated with AIDS (acquired immune deficiency syndrome), ARC (AIDS-related complex) and related diseases. A distinguishing feature of HIV is its selective cytotoxicity for helper T lymphocytes. Severe and diverse aberrations of the immune system significantly reduce the host defense against various opportunistic infections, resulting finally in a host death.

Nowadays, many anti-HIV agents including Krestin and Lentinan have been isolated from plants and chemically synthesized. However, the effect of most of these agents are generally weak and they have severe side effects.

In order to explore new type of anti-HIV substance, the present inventors have compared the anti-HIV activity of various plant components. The present inventors have found potent anti-HIV activity in the antitumor substances obtained from aqueous alkaline extract of pine cone. The substances with the most potent anti-HIV activity was named as KS-6 and KS-7.

SUMMARY OF THE INVENTION

An object of the present invention is to provide two plant-derived high molecular weight substances which have potent anti-HIV activity.

Another object of the present invention is to provide anti-HIV agents having as active components the above-mentioned high molecular weight substances.

Still another object of the present invention is to provide a method for obtaining the high molecular weight anti-HIV substances from pine cones.

The anti-HIV agents in the present invention are characterized in that said agents which contain alkaline-water extracts of various pine cones such as *Pinus parviflora Sieb. et Zucc.*, especially high molecular weight anti-HIV substances of this extract. The high molecular weight anti-HIV substances described above can be obtained by extraction of the pine cone with alkaline water.

Other objects and characteristics of the invention will become apparent from further disclosure of the invention to be made in the following detailed description of preferred embodiment, with reference to the accompanying drawings.

DETAILED DESCRIPTION OF THE INVENTION

Figure 1:
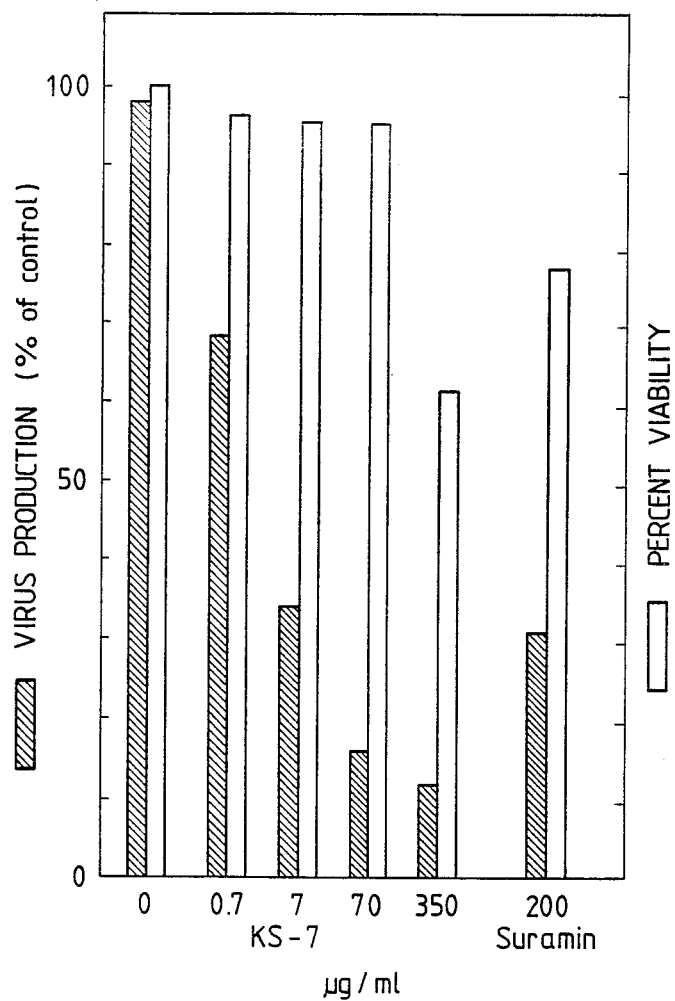
FIG. 1 shows dose-dependent inhibition by KS-7 of viral production in CEM cells chronically infected with HIV.

Pine cones of various Pine trees such as *Pinus parviflora Sieb. et Zucc., Pinus densiflora Sieb. et Zucc.*, and *Pinus thunbergii Parl.*, can be used for the preparation of anti-HIV substances. It is preferable to use *Pinus parviflora Sieb. et Zucc.* due to an of active substances. Pine cones collected at summer season are enriched in floating fatty materials, which might disturb further purification. Therefore the pine cones should be collected in October when active substances accumulate in abundance.

The substances with a certain extent of activity can be extracted from pine cone by hot water extraction. However alkaline water extraction is more effective than hot water extraction to obtain larger amounts of the active substances the pine cone. Either alkaline extracts or further fractionated materials can be used as effective anti-HIV substances. The present inventors presumed that substances which are contained in this extract and used as active ingredients are high molecular weight substances. The most potent substances were named as KS-6 and KS-7.

Alkaline water extracts used in this invention can be prepared by directly extracting a pine cone with aqueous alkaline solution such as aqueous NaOH. It is preferable, however, to obtain alkaline water extracts from a pine cone in which oils and hot-water extractable materials have been removed by extensive alcohol and boiling water washing before alkaline water extraction.

Either organic bases or inorganic bases can be used as alkaline substances for extraction media. The pH in aqueous alkaline solution is preferable to be more than 8.0; most preferably pH being 9.0 to 13.0.

The extracted solution should be concentrated to desired concentration, if needed, neutralized with appropriate acid and then lyophilized to give appropriate concentrated solution or solid. These can be used as active components without further fractionation. Alternatively, the concentrate can be separated into precipitate and supernatant by some appropriate methods such as centrifugation. KS-6 can be obtained from precipitate by reextraction with alkaline water, and KS-7 from supernatant by ethanol precipitation.

The present invention will be explained by the following one example, however, the invention will not be restricted to this example.

PURIFICATION PROCEDURE OF KS-6 AND KS-7

500g of pine cones was washed succesively, twice with about 5 liters of methanol, and twice with 85% ethanol for 4 hours with reflux, and then extracted for 6 hours, 3 times with boiling water. The residue was extracted twice with 5 liters of 1% sodium hydroxide aqueous solution for 6 hours at room temperature. After removal of insoluble materials by filtration through gauze, the pH of the filtrate was adjusted to 5.0 with acetic acid. The precipitate was collected by centrifugation for 20 minutes at 10000 xg at 4° C., dissolved in a small volume of 1% sodium hydroxide aqueous solution, centrifuged to remove insoluble materials and the supernatant was neutralized with acetic acid. The obtained substance is KS-6. The remaining supernatant was precipitated with one volume of ethanol to obtain KS-7. Both KS-6 and KS-7 were dialyzed against distilled water and lyophilized. Yield of these substances KS-6 and KS-7 was about 0.5% and 1%, respectively.

ANALYTICAL PROCEDURES

Neutral sugar composition was analyzed by gas-liquid chromatography of trimethylsilyl derivatives of methyl glucosides obtained by methanalysis in methanolic HCl for 16 hours at 65° C. Neutral sugar content was also determined by the phenol-sulfuric acid method. Uronic acids were analyzed by gas-liquid chromatography of trimethylsilyl derivatives after their conversion to aldonolactone. Uronic acids content was determined by the carbazole method. Carbon, hydrogen, nitrogen and sulfur content was determined by element analyzer.

ENDOTOXIN ASSAY

The presence of endotoxin was determined by the Endospecy (Endotoxin Specific Test, Seikagaku Kogyo, Ltd., Japan) with Escherichia coli 0111:B4 endotoxin as a standard.

HIV INFECTION TO T CELL

The CEM cell used was a T cell line derived from human leukemia patient. The virus used was HIV N.Y. strain.

CEM cells were infected by addition with HIV-carrying culture medium. Infectivity of the virus released into the culture medium was assayed with reverse transcriptase (RT) activity and p24 antigen capture method.

KS-6 has a dark brownIsh color, with an absorption shoulder at 260–280 nm. It easily dissolves in water, and mixtures of water and alcohol, or acetone. It contains carbon (43.2wt%), hydrogen (4.0wt%), nitrogen (2.6wt%) and no sulfur. KS-6 contains also neutral sugars (11.0wt%) consisting of fucose (9.4mol%), mannnose (19.0mol%), galactose (44.7mol%) and glucose (26.9mol%), and a negligible amount of uronic acid (1.7wt%). The molecular weight determined by gel filtration under alkaline condition was 10 kD.

KS-7 also has brownish color, with an absorption shoulder at 260–280 nm. It easily dissolves in water, but tends to precipitate in physiological saline and the mixtures of water and alcohol, or acetone. It has carbon (33.55wt%), hydrogen (4.23wt%), and undetectable amount of nitrogen and sulfur. KS-7 contains also neutral sugars (39.5wt%) consisting of arabinose (16.5mol%), mannose (16.2mol%), galactose (39.3mol%) and glucose (26.0mol%), and abundant uronic acid (58.2wt%). The contamination of endotoxin was around 0.0025%. The molecular weight determined by gel filtration under alkaline condition was 10–200 kD.

ANTI-HIV ACTIVITY OF KS-6 AND KS-7

1. Effect of KS-7 on chronic HIV infection

Figure 2:
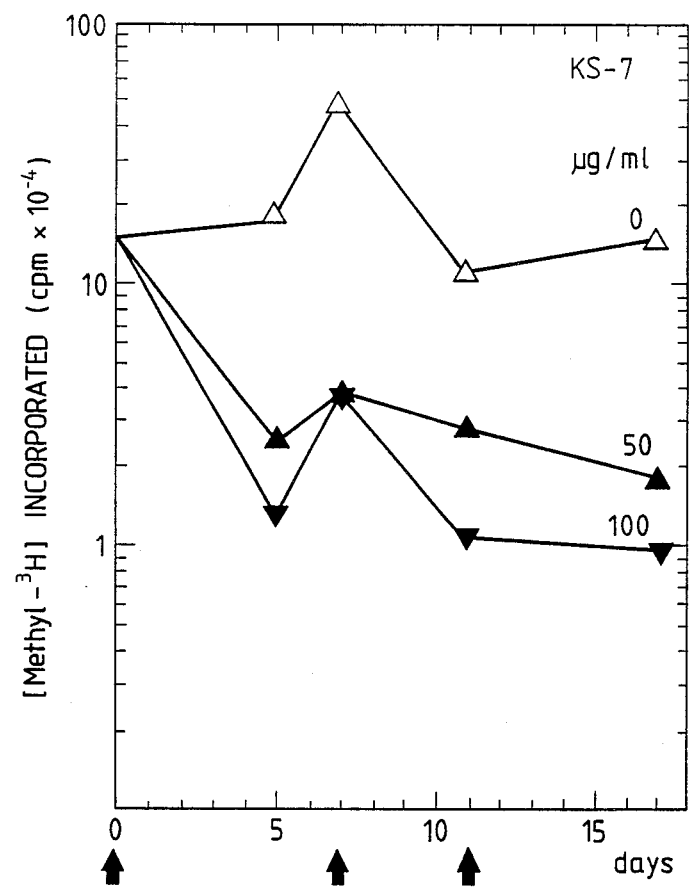
FIG. 2 shows time course of inhibition by KS-7 of viral replication in CEM cells chronically infected with HIV.

A clone of the CEM T cell line was cultured for long period with HIV at low virus infection ratio. The chronically infected cells were incubated for 1 week with various concentration of KS-7 (0–350 μg/ml). At various time points thereafter HIV production in culture supernatants was measured by RT method. As shown in FIG. 1, HIV replication was reduced by 66% by addition of KS-7 at concentration of as low as 7 μg/ml. KS-7, at concentration of more than 70 μg/ml, inhihIt HIV replication by more than 85%. Viability of CEM cells was not affected by treatment with 70 μg/ml of KS-7. A similar degree of inhibition of HIV replication was observed in cells treated with 200 μg/ml suramine, a potent inhibitor of retrovial RT. However, this concentration of suramine reduced the viability of CEM cells to 78%. The time course of the inhibition of HIV replication by KS-7 was next investigated. The chronically infected CEM cells were treated with 50 pg/ml or 100 μg/ml KS-7 for 5, 7, 10, or 17 days and the viral RT activity recovered from the culture supernatant was determined as shown in FIG. 2. RT activity found in supernatants of the treated cells was at any time points inhibited by about 90%. This indicates that KS-7 inhibit viral production.

It should be noted that the cells were diluted 1:5 and supplemented with fresh medium containing KS-7 at the time indicated by arrows, and the RT activity (ordinate) was plotted in log scale in FIG. 2.

2. Effect of KS-6 on acute HIV infection

Figure 3:
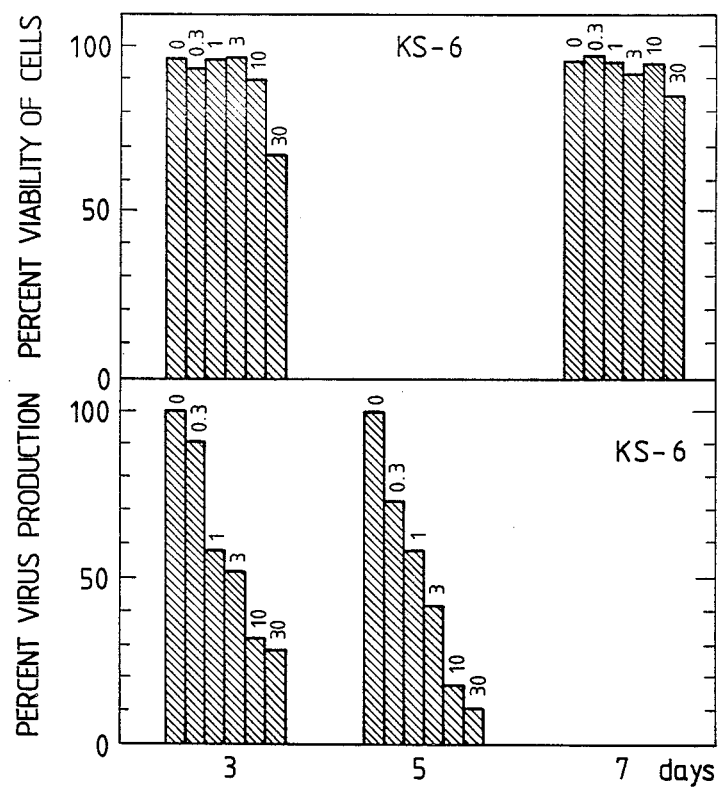
FIG. 3 shows effect of KS-6 added just after the HIV infection.

Next, the ability of KS-6 to inhibit virus replication in acute infection with HIV was investigated. The CEM cells were infected with HIV at high virus concentration. After viral adsorption, the cells were washed 3 times with medium and maintained at $5 \times 10^5$ cells/ml in medium supplemented with various concentrations of KS-6 (ranged from 0–30μg/ml). After incubation for 3 to 7 days, concentration of HIV p24 antigen in the culture supernatants was determined by a commercially available p24 antigen capture assay (Abbot's Lab.). As shown in FIG. 3, the antiviral activity was induced by KS-6 at more than 0.3 μg/ml. Higher concentration of KS-6 ("3 pg/ml" or "30 μg/ml") inhibited HIV replication by 50% and 88%, respectively. The viability of CEM cells was not significantly affected at any of these concentrations.

3. Effect of CEM cell pretreatment by KS- 6 or KS-7

Figure 4:
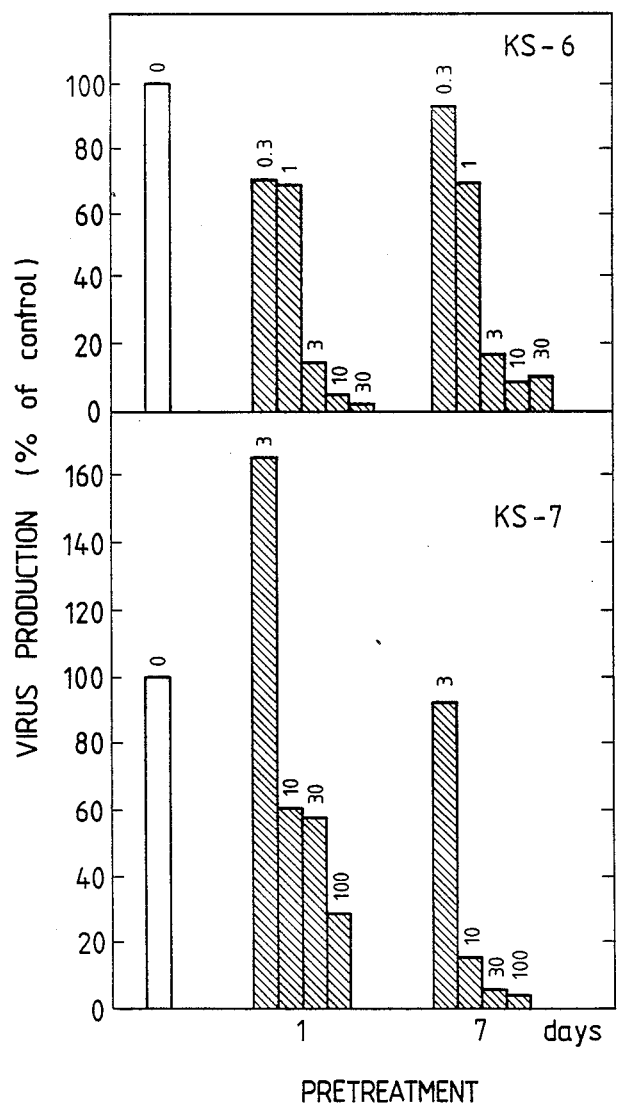
FIG. 4 shows effect of pretreatment wIth KS-6 or KS-7 on HIV replication.

It was Investigated whether pretreatment of CEM cells with KS-6 or KS-7 could enhance the inhibition of HIV replication. CEM cells were Pretreated for 1 or 7 days with various concentrations of KS-6 (0.3–30 μg/ml) or KS-7 (3–100 μg/ml). After washing, the cells were infected with HIV virus at high virus concentration, and maintained in medium containing the same concentrations of KS-6 or KS-7 used in pretreatment. After 5 days incubation, the concentratIon of p24 in culture supernatant was determined by p24 antigen capture method. As seen in FIG. 4, a reduction of viral titer was observed in CEM cell cultures pretreated with 0.3 μg/ml of KS-6. An 80–95% reduction of HIV replication was attained by KS-6 at the concentrations of 3 and 30 μg/ml, respectively. In contrast, antiviral activity of KS-7 was slightly weaker than that of KS-6. The anti-HIV activity of KS-7 was detected at more than 10 μg/ml, and 95% inhibition of HIV replication was achieved by KS-7 at 30–100 μg/ml.

The present data demonstrate that antitumor substances KS-6 and KS-7, prepared from alkaline water extracts of pine cone effectively inhibit HIV replication, and the antivial activity of these agents is augumented by pretreatment of the target cells with these agents before HIV infection. A distinguishing feature of human immunodeficiency virus (HIV) is its selective cytotoxicity for helper T lymphocytes. Infection in vivo is manifested by severe and diverse abberations of immune system and causes death. As descrived above, KS-6 and KS-7 of the present invention have potent anti-HIV activity, as well as their immunopotentiating activity manifested by activation of human peripheral blood monocytes and polymorphonuclear cells. Therefore, it is highly probable that these agents might improve the condition of AIDS patients and its effect might be augumented by combinational treatment with other chemotherapeutic agents (e.g. azido-thymidine, dideoxycytidine, suramine).

What is claimed is:

1. Anti-HIV agents containing as active components extract which has been extracted with alkaline water from pine cone.

2. Anti-HIV agents as claimed in claim 1, wherein said extract is extracted from Pinus parviflora Sieb. et Zucc pine cone.

3. Anti-HIV agents as claimed in claim 1, wherein the active components are at least one member selected from the group consisting of KS-6 and KS-7 which are contained in the extract which has been extracted with alkaline water from pine cone.

4. Anti-HIV agent as claimed in claim 3, wherein said member is KS-6, which has a brownish color with an absorption soulder at 260–280 nm, which dissolves in water, and mixtures of water and alcohol or acetone, and is composed of 43.2% wt% arbon, 4.0 wt % hydrogen, 2.6 wt% nitrogen, and has a molecular weight of about 10 kD by gel filtration under alkaline condition, said KS-6 being obtained from the precipitate from alikaline-water extract of pine cone at pH 5.

5. Anti-HIV agent as claimed in claim 3, wherein said member is KS-7, having a brownish color with an absorption shoulder at 260–280 nm, capable of being dissolved well in water, but tending to precipitate in physiological saline and mixtures of water and alcohol or acetone, and is composed of 33.5 wt% carbon, 4.23 wt 5% hydrogen and undetectable amount of nitrogen and sulfate, and having a molecular weight of 10–200 kD under alkaline condition by gel filtration, said KS-7 being from recovered from supernatant fraction of alkaline water extracts by ethanol precipitation after adjustment to pH 5.

6. The anti-HIV agent of claim 1 wherein said extract has been extracted with alkaline water having a pH of at least 8.

7. The anti-HIV agent of claim 6 wherein said alkaline water has a pH of from 8 to 13.

8. A method for producing KS-6 comprising the steps:
   extracting a pine cone with 1% NaOH after removal of alcohol and hot water extractable materials, precipitating the NaOH extract at pH 5, predissolving the precipitate by 1% NaOH to remove impurities and extensively dialyzing against distilled water.

9. An anti-HIV composition containing an effective amount of KS-6 as obtained according to claim 8, and a suitable carrier or diluent.

10. A method for producing KS-7 comprising the steps:
    extracting a pine cone with 1% NaOH after removal of alcohol and hot water extractable materials,
    precipitating the NaOH extract with an equal volume of ethanol, and
    extensively dialyzing the precipitate against water.

11. An anti-HIV composition containing an effective amount of KS-7 obtained according to claim 10, and a suitable carrier or diluent.

* * * * *